(12) United States Patent
Zhou

(10) Patent No.: US 12,220,299 B2
(45) Date of Patent: Feb. 11, 2025

(54) ADJUSTABLE EAR SHAPING MECHANISM

(71) Applicant: Guangzhou T.K Medical Instrument Co., Ltd., Guangzhou (CN)

(72) Inventor: Xing Zhou, Guangzhou (CN)

( * ) Notice: Subject to any disclaimer, the term of this patent is extended or adjusted under 35 U.S.C. 154(b) by 347 days.

(21) Appl. No.: 17/741,336

(22) Filed: May 10, 2022

(65) Prior Publication Data

US 2022/0265474 A1 Aug. 25, 2022

Related U.S. Application Data

(63) Continuation of application No. PCT/CN2020/127421, filed on Nov. 9, 2020.

(30) Foreign Application Priority Data

Nov. 12, 2019 (CN) .......................... 201911101712.1

(51) Int. Cl.
*A61F 11/06* (2006.01)
*A61F 11/00* (2022.01)

(52) U.S. Cl.
CPC ................................... *A61F 11/00* (2013.01)

(58) Field of Classification Search
CPC .......... A61F 11/14; A61F 11/06; A61F 11/12; A61B 17/0487; A45D 44/22
See application file for complete search history.

(56) References Cited

U.S. PATENT DOCUMENTS 2,339,572 A * 1/1944 Jurovaty ............. A61F 5/05891
606/204.15
6,517,557 B1 * 2/2003 Sorribes .................... A61F 5/01
606/1

(Continued)

FOREIGN PATENT DOCUMENTS

| CN | 109893317 A | 6/2019 |
|---|---|---|
| CN | 209332470 U | 9/2019 |

(Continued)

OTHER PUBLICATIONS

Zhou, Xing, International Preliminary Report on Patentability and Written Opinion, PCT/CN2020/127421, Jan. 27, 2021, 14 pages.

(Continued)

*Primary Examiner* — Camtu T Nguyen
(74) *Attorney, Agent, or Firm* — Morgan, Lewis & Bockius LLP

(57) ABSTRACT

An adjustable ear shaping mechanism of the present application includes a base, an ear back support, and an upper cover. An opening is provided on the base, and the opening can allow an ear to pass therethrough. The ear back support is movably disposed in the opening, and supports an auricle from the back of the ear according to a part needing orthopedics. The upper cover is detachably connected to the base. An object-containing space is formed between the upper cover, the base, and the ear back support, and the ear is placed in the object-containing space. In a clinical use process, the ear back support may be disposed at a corresponding malformed part behind the ear according to a malformed part of the ear, the auricle is supported from the back of the ear, orthopedic requirements of different parts can be met, and clinical use is very convenient. In particular, due to a surface contact three-dimensional space traction orthopedic manner of an auricle former, not only a pressure intensity of a contact part is reduced, but also an intended aim of orthopedics can be achieved by a small force, so that clinical use is safer, and an orthopedic effect is better.

15 Claims, 10 Drawing Sheets

(56) References Cited

U.S. PATENT DOCUMENTS

| | | | |
|---|---|---|---|
| 8,136,530 B2 * | 3/2012 | Byrd | A61F 11/00 606/204.15 |
| 11,185,446 B2 * | 11/2021 | Bartlett | A61F 5/01 |
| 2012/0179078 A1 * | 7/2012 | Koehler | A61F 11/20 602/2 |
| 2012/0185043 A1 | 7/2012 | Byrd | |

FOREIGN PATENT DOCUMENTS

| | | |
|---|---|---|
| CN | 209474958 U | 10/2019 |
| CN | 211583815 U | 9/2020 |

OTHER PUBLICATIONS

Zhou, Xing, International Search Report, PCT/CN2020/127421, dated Jan. 27, 2021, 4 pages.

Zhou, Xing, Communication Pursuant to Rules 161(2), and 162 EPC, EP20887283.3, Jun. 22, 2022, 3 pgs.

\* cited by examiner

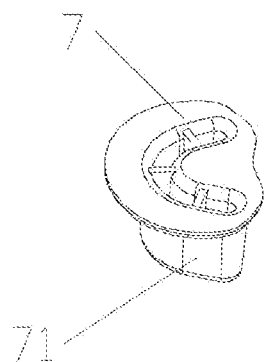
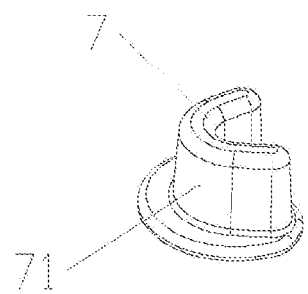
FIG. 5  FIG. 5-1
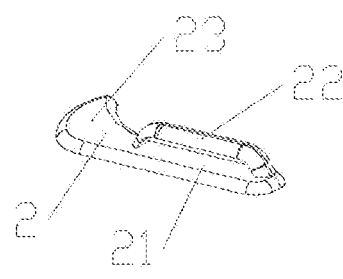
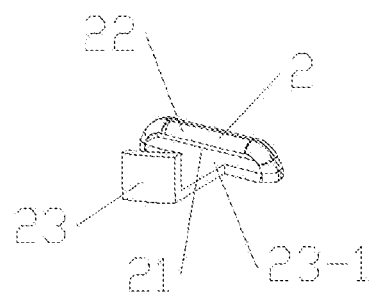
FIG. 6  FIG. 6-1

ADJUSTABLE EAR SHAPING MECHANISM

CROSS-REFERENCE TO RELATED APPLICATIONS

This application is a continuation application of PCT Patent Application No. PCT/CN2020/127421, entitled "ADJUSTABLE EAR SHAPING MECHANISM" filed on Nov. 9, 2020, which claims priority to Chinese Patent Application No. 201911101712.1, entitled "ADJUSTABLE EAR SHAPING MECHANISM" and filed with the China National Intellectual Property Administration on Nov. 12, 2019, both of which are incorporated herein by reference in their entirety.

FIELD OF THE INVENTION

The present application relates to a surgical medical instrument, and especially, to an adjustable ear shaping mechanism used during ear orthopedics.

BACKGROUND OF THE INVENTION

An ear is formed by a cartilage covered by skin, and a normal ear shape needs to be provided with a helix, a scapha, a triangular fossa, an antihelix, an auricular concha, a tragus, an antitragus, and an earlobe. The helix needs to be provided with a full rolled rim, the antihelix needs to be provided with a full curved shape, and a Y-shaped antihelix angle is formed, to form the triangular fossa. A cavity of auricular concha formed between the antihelix, the antitragus, the tragus, and a crus of helix is a position used for placing an earplug.

However, according to statistics, there is an extremely high incidence rate of neonatal ear malformation or deformity, and in some countries and regions, even nearly half of newborns undergo ear malformations or deformations. The ear malformations or deformations include various forms such as prominent ears, cup ears, lop ears, Stahl's ears, cryptotia, and helix malformations. Malformation may occur in various parts such as the helix, the antihelix, and the cavity of auricular concha.

At present, the neonatal ear malformation or deformity can be treated by orthopedics with an orthosis. However, the malformed or deformed part is uncertain, and therefore the orthopedic part of the orthosis is also uncertain. Therefore, the orthosis needs to be further improved to meet orthopedics of different malformed parts.

SUMMARY

An adjustable ear shaping mechanism of the present application provides a special design in which an ear back support may be adjusted for different supporting positions. In clinical use, the ear back support is placed in different positions according to a specific morphological feature of an ear malformation, to adapt to orthopedic needs of different malformed parts.

The present application provides an adjustable ear shaping mechanism. The adjustable ear shaping mechanism 100 includes a base 1, an ear back support 2, and an upper cover 3, where A. an opening 11 is provided on the base 1, and the opening 11 allows an ear 4 to pass therethrough;

B. the ear back support 2 is movably disposed in the opening 11, and supports an auricle from the back of the ear 4 according to a part needing orthopedics; and C. the upper cover 3 is detachably connected to the base 1, and an object-containing space 5 is formed between the upper cover 3, the base 1, and the ear back support 2.

The ear back support 2 of the adjustable ear shaping mechanism of the present application is designed as movable. In a clinical use process, the ear back support 2 may be disposed at a corresponding malformed part behind the ear according to a malformed part of the ear, and support the auricle from the back of the ear 4. During clinical use, the ear back support 2 is fixed at the corresponding malformed part, then the ear 4 extends from the opening 11 of the base, and the base 1 is fixed on a periphery the ear 4. Then, the upper cover 3 covers the base 1, and the ear 4 is fixed in the object-containing space 5, so that an orthopedic treatment can be performed.

The base 1 is fixed on skin of the periphery of the ear 4 by pasting. The base 1 may be pasted on the skin of the periphery of the ear 4 by a medical tape, and preferably a double-sided medical tape 9 may be selected for pasting. One side is pasted on the bottom of the base 1, and the other side is pasted on the skin. When needing to be replaced, the double-sided medical tape 9 can be torn off, and the use process is very convenient. Certainly, in a practical application, those skilled in the art may also use other fixing manners to fix the base 1 on the periphery of the ear as required.

The ear back support 2 may be pasted on the skin behind the ear 4 for fixing. The ear back support 2 may be pasted on the skin behind the ear 4 by the double-sided medical tape 9. When the part needing orthopedics changes, the double-sided medical tape 9 can be torn off to re-fix the ear back support 2 on a different part, which may be adjusted according to a treatment process during clinical use.

The ear back support 2 may be connected onto a side wall 12 of the base 1. The ear back support 2 may further be connected onto the side wall 12 of the base 1, and move along the side wall 12 to adjust a position of the ear back support 2.

The ear back support 2 may be connected onto the side wall 12 of the base 1 by pasting or inlaying. In particular, by inlaying connection, the ear back support 2 may be easily inlaid in different connecting grooves 12-1, which is very convenient for clinical use.

An elastic groove 21 is provided on the ear back support 2. The ear back support 2 is arranged behind the ear 4, and the base 1 is fixed at the front of the ear 4 by the upper cover 3. A space height behind the ear is different for everyone. If the space height behind the ear is small, and an excessively large height of the ear back support 2 is likely to cause ischemic necrosis of the ear under an external force, resulting in an accidental injury during an orthopedic process. The elastic groove 21 may be contracted under the external force and reset after the external force is released. Therefore, when the space height behind the ear is small, under the external force, the elastic groove 21 is compressed, and the space increases, so that the elastic groove may adapt to different space heights behind the ear, and clinical use is safer.

The adjustable ear shaping mechanism 100 further includes a helix former 6. The helix former 6 may be used for helix orthopedics, and especially suitable for forming a rolled rim of the helix.

The helix former 6 includes a forming groove 61 and a fixing portion 62, and the fixing portion 62 and the base 1 are connected. The forming groove 61 is inlaid on the helix to perform orthopedics on the rolled rim of the helix. The fixing portion 62 and the base 1 are connected, which may prevent the helix former 6 from moving and maintain the stability of the orthopedic process.

The fixing portion 62 is connected to the base 1 by pasting or inlaying. The fixing portion 62 may be fixedly connected to the base 1 by pasting, inlaying, or a combination of pasting and inlaying. In a practical application, those skilled in the art may further design different connection manners as required. The applicant does not give specific examples herein, which do not depart from the protection scope of the present application.

The adjustable ear shaping mechanism 100 further includes an auricular concha former 7. The auricular concha former 7 is designed according to a shape feature of a cavity of auricular concha, and can be used for orthopedics of the cavity of auricular concha. During clinical use, a shaping end 71 of the auricular concha former 7 is plugged into an ear canal, and then the auricular concha former 7 is fixed in the object-containing space 5 by the upper cover 1.

The adjustable ear shaping mechanism 100 further includes an auricle former 8, and the auricle former 8 is arranged at the front of the ear 4.

The auricle former 8 and the ear back support 2 are matched with each other, and a space therebetween forms a forming space of the ear 4.

The auricle former 8 includes a helix forming mechanism 81, and/or an antihelix forming mechanism 82, and/or a triangular fossa forming mechanism 83, and/or an auricular concha forming mechanism 84, and/or a tragus forming mechanism 85, and/or an antitragus forming mechanism 86.

One or more of the foregoing forming mechanisms may be arranged on the auricle former 8 according to a shape feature of a normal ear. The space between the auricle former 8 and the ear back support 2 is in the shape of the normal ear. Overall shaping may be performed on the ear 4 through mutual cooperation between the auricle former 8 and the ear back support 2, so that the orthopedics on the whole ear can be completed at a time in the clinical use process. The helix forming mechanism 81, the antihelix forming mechanism 82, the triangular fossa forming mechanism 83, the auricular concha forming mechanism 84, the tragus forming mechanism 85, and the antitragus forming mechanism 86 are designed according to morphological features of the normal ear. Therefore, in the orthopedic process, the helix forming mechanism 81, the antihelix forming mechanism 82, the triangular fossa forming mechanism 83, the auricular concha forming mechanism 84, the tragus forming mechanism 85, and the antitragus forming mechanism 86 can fit the shape of each part to form surface contact, to change an orthopedic manner in which the helix is partially expanded and pulled outwards in the prior art into a surface contact three-dimensional space traction orthopedic manner. In this way, a pressure intensity at a contact part is reduced, and tissue compression and necrosis are less likely to occur. In addition, for the manner of space multi-point traction, only a very small force is needed to achieve an intended aim of orthopedics, a clinical use process is safer, and an orthopedic effect is better.

The auricle former 8 and the upper cover 3 may be integrally made. The auricle former 8 may be disposed separately and then covered by the upper cover 3, or may be formed as a whole with the upper cover 3. To ensure auditory sensation of children patients, through holes are provided on the auricle former 8 and the upper cover 3 to ensure sound conduction.

The base 1 is made of a flexible medical material.

The flexible material is silicone, rubber, thermoplastic elastomer (TPE), or thermoplastic polyurethane (TPU) elastomer rubber.

The adjustable ear shaping mechanism of the present application is usually clinically used for ear orthopedics of newborns, and skin of the newborns is very delicate and sensitive. Therefore, the base 1 in contact with the skin is made of the medical flexible material to ensure comfort. Preferably, the adjustable ear shaping mechanism of the present application is made of the medical flexible material as a whole.

During clinical use, first, according to a morphological feature of an ear malformation, a position for mounting the ear back support 2 is selected, and then the ear back support 2 is pasted on skin by the double-sided medical tape 9. Then the base 1 is mounted on the periphery of the ear 4, and the ear 4 extends from the opening of the base 1. In addition, the base 1 is fixed on the skin of the periphery of the ear 4 by the double-sided medical tape 9, and is covered by the upper cover 3. The object-containing space 5 is formed between the upper cover 3, the base 1, and the ear back support 2, and the ear 4 is placed in the object-containing space 5. Meanwhile, the upper cover 3 stretches the base 1 around, to realize traction and orthopedics of the ear 4.

The adjustable ear shaping mechanism of the present application includes the base 1, the ear back support 2, and the upper cover 3. The base 1 includes the opening 11, and the opening 11 allows the ear 4 to pass therethrough. The ear back support 2 is movably disposed in the opening 11, and supports the auricle from the back of the ear 4 according to the part needing orthopedics. The upper cover 3 is detachably connected to the base 1. The object-containing space 5 is formed between the upper cover 3, the base 1, and the ear back support 2, and the ear 4 is placed in the object-containing space 5. In the clinical use process, the ear back support 2 may be disposed at the corresponding malformed part behind the ear according to the malformed part of the ear, and support the auricle from the back of the ear 4, orthopedic needs of different parts can be met, and clinical use is very convenient. In particular, in the surface contact three-dimensional space traction orthopedic manner of the auricle former 8, not only the pressure intensity of the contact part is reduced, but also the small force can achieve the intended aim of orthopedics. The clinical use is safer, and the orthopedic effect is better.

BRIEF DESCRIPTION OF THE DRAWINGS

FIG. 1-1 is a bottom view of FIG. 1.

FIG. 1-2 is a schematic three-dimensional structural diagram of FIG. 1 with an upper cover being removed.

FIG. 1-3 is a cross-sectional view of FIG. 1-2.

FIG. 1-4 is an exploded view of FIG. 1.

FIG. 2 is a schematic three-dimensional structural diagram of a closed adjustable ear shaping mechanism of the present application with an ear back support being pasted on a side wall.

FIG. 2-1 is a top view of FIG. 2.

FIG. 2-2 is a schematic three-dimensional structural diagram of the ear back support of FIG. 2.

FIG. 3 is a schematic three-dimensional structural diagram of a closed adjustable ear shaping mechanism of the present application with an ear back support being inlaid on a side wall.

FIG. 3-1 is a schematic three-dimensional structural diagram of the ear back support of FIG. 3.

FIG. 4 is a schematic three-dimensional structural diagram of a closed adjustable ear shaping mechanism of the present application including a helix former.

FIG. 4-1 is a schematic three-dimensional structural diagram of the helix former of FIG. 4.

FIG. 5 is a schematic three-dimensional structural diagram of an auricular concha former.

FIG. 5-1 is a schematic three-dimensional structural diagram of FIG. 5 when viewed from the bottom.

FIG. 6 is a schematic three-dimensional structural diagram of a paste-type ear back support including an elastic groove.

FIG. 6-1 is a schematic three-dimensional structural diagram of an inlay-type ear back support including an elastic groove.

FIG. 8-1 is a partial exploded view of FIG. 8.

FIG. 8-2 is a view depicting a working principle with an upper cover of FIG. 8 being removed.

In the foregoing accompanying drawings:

100 is an adjustable ear shaping mechanism of the present application.

1 is a base, 2 is an ear back support, 3 is an upper cover, 4 is an ear, 5 is an object-containing space, 6 is a helix former, 7 is an auricular concha former, 8 is an auricle former, and 9 is a double-sided medical tape.

11 is an opening, 12 is a side wall, 12-1 is a connecting groove, and 12-2 is a limiting groove.

21 is an elastic groove, 22 is a support portion, 23 is a connecting end, and 23-1 is a connecting bridge.

61 is a forming groove, 62 is a fixing portion, 62-1 is a clamping groove, 62-11 is an outer leg, and 62-12 is an inner leg.

71 is a shaping end.

81 is a helix forming mechanism. 82 is an antihelix forming mechanism, 83 is a triangular fossa forming mechanism. 84 is an auricular concha forming mechanism, 85 is a tragus forming mechanism, and 86 is an antitragus forming mechanism.

DESCRIPTION OF EMBODIMENTS

Embodiment 1: Adjustable Ear Shaping Mechanism of the Present Application

Figure 1:
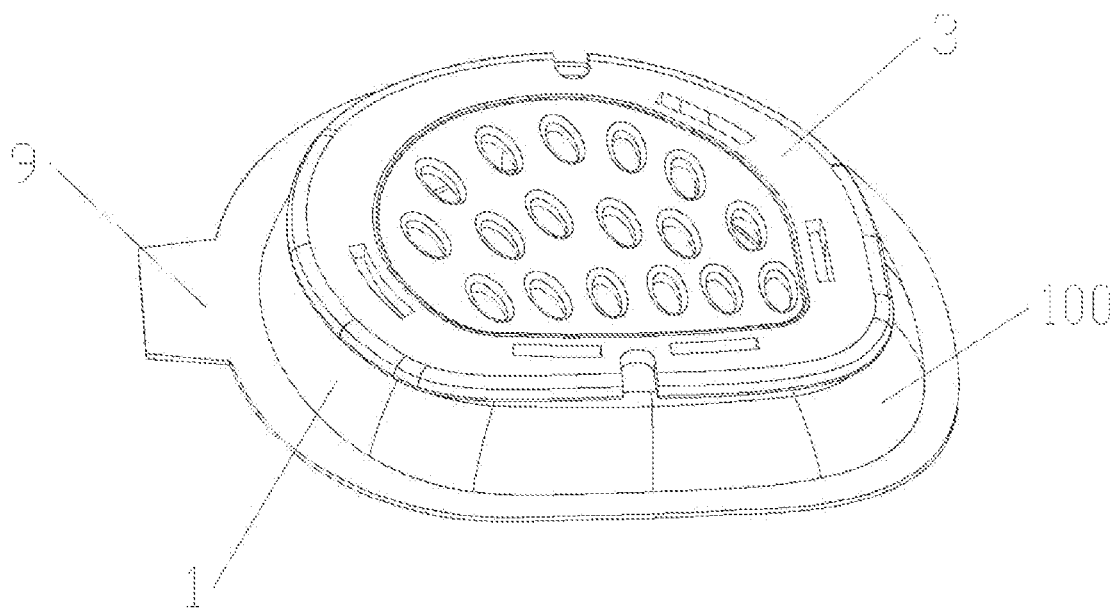
FIG. 1 is a schematic three-dimensional structural diagram of a closed adjustable ear shaping mechanism of the present application.
Figure 1:
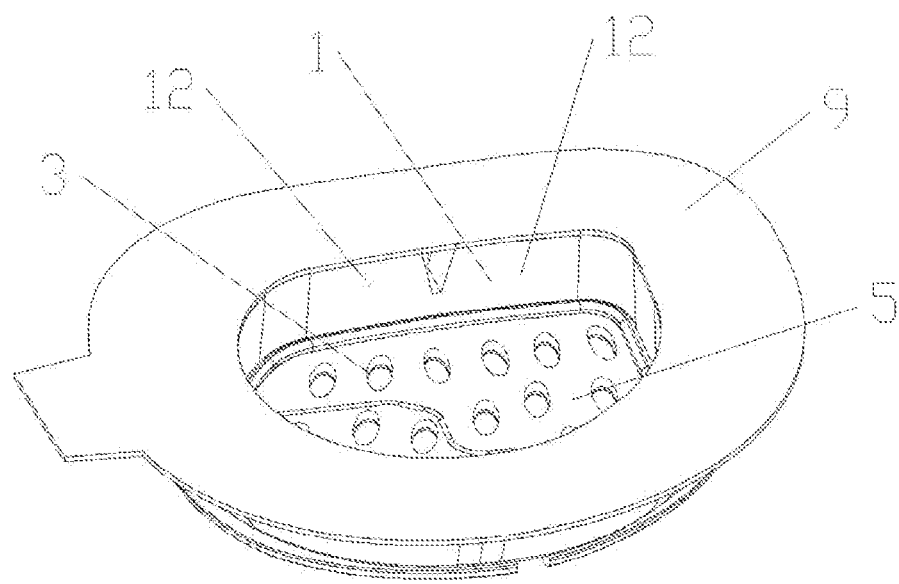
Figures 1, 2:
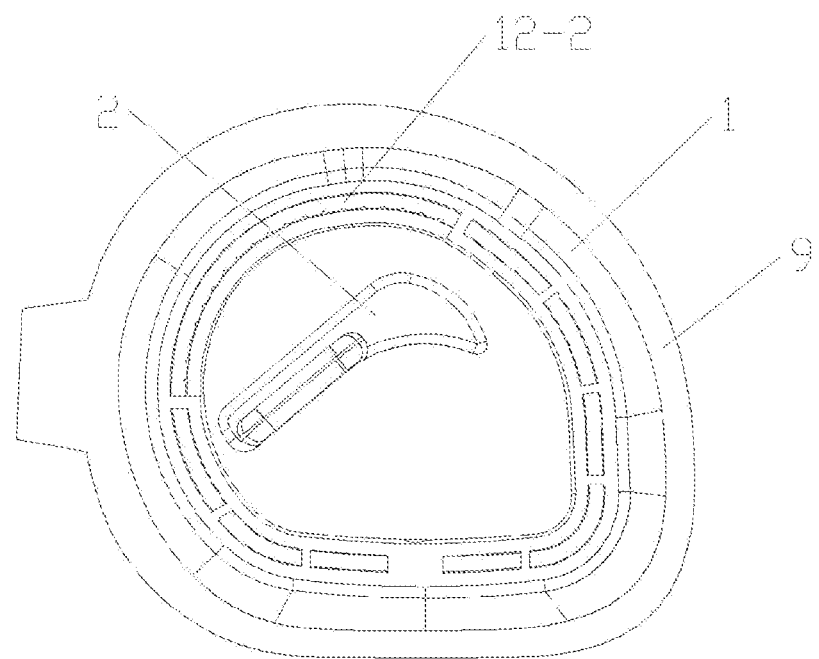
Figures 1, 2, 3:
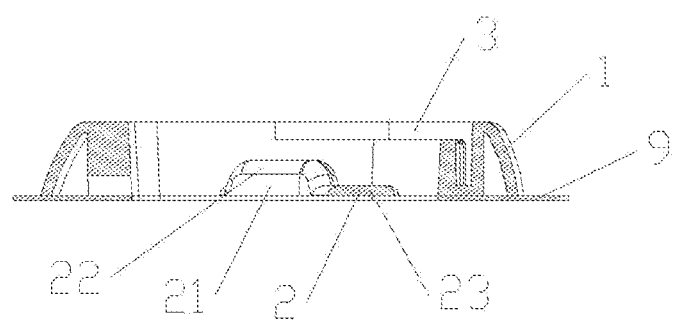
Figures 1, 2, 3, 4:
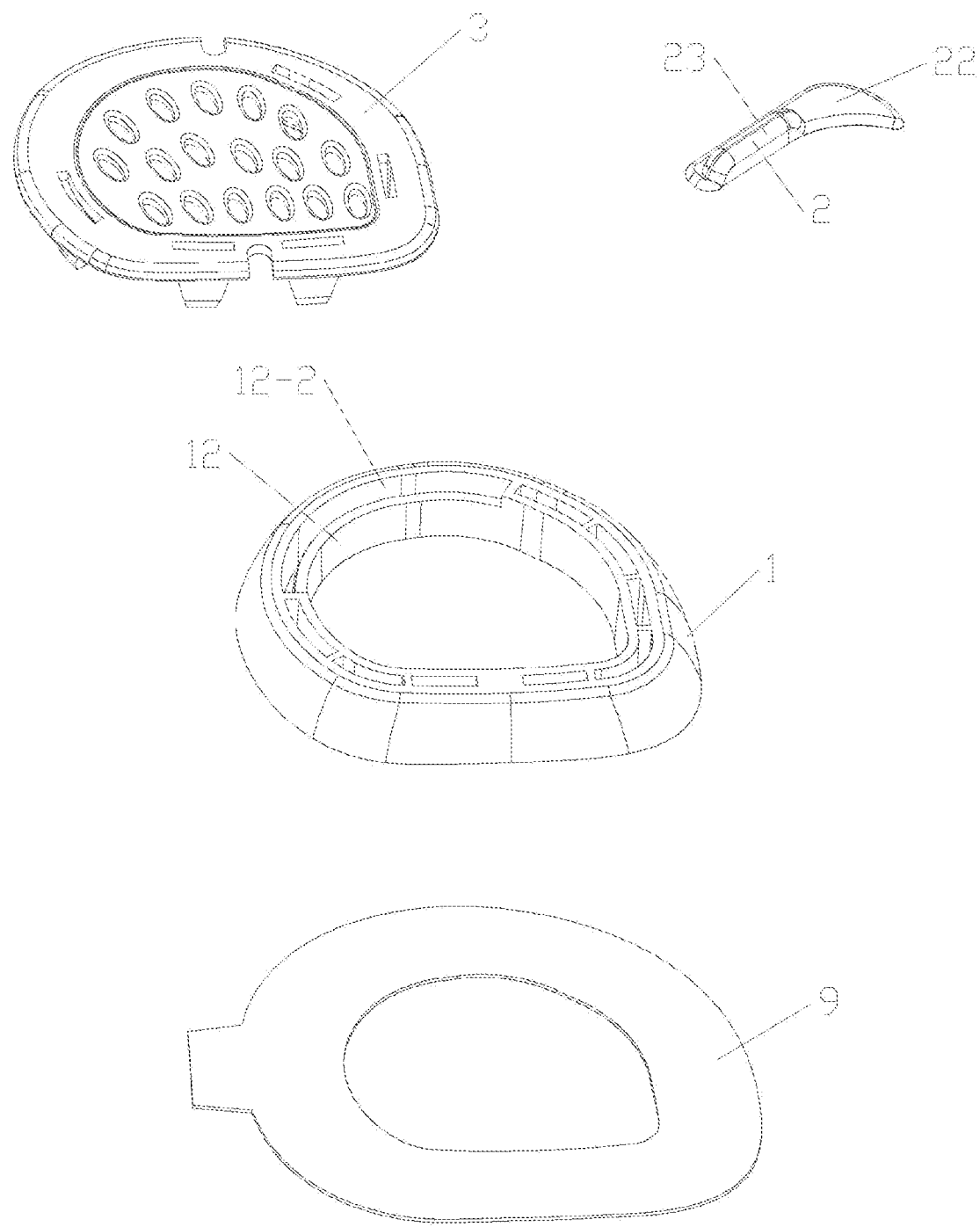
Figure 2:
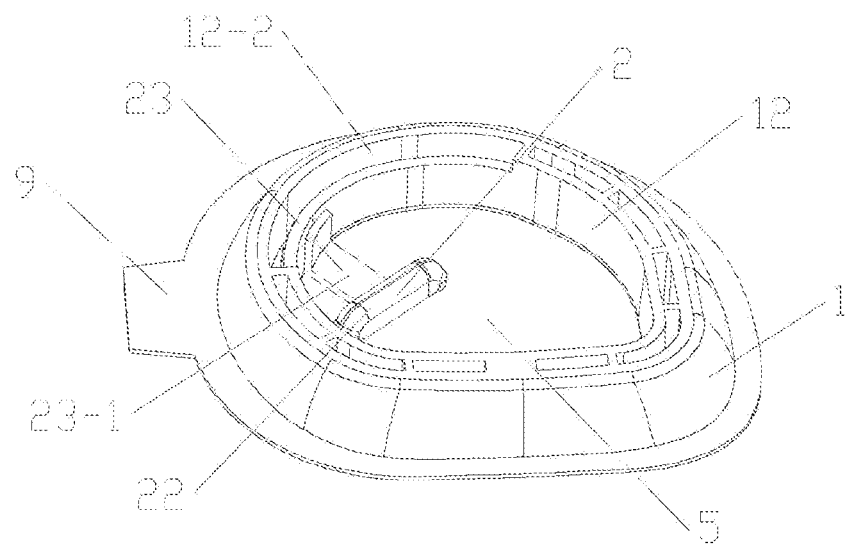
Figures 1, 2:
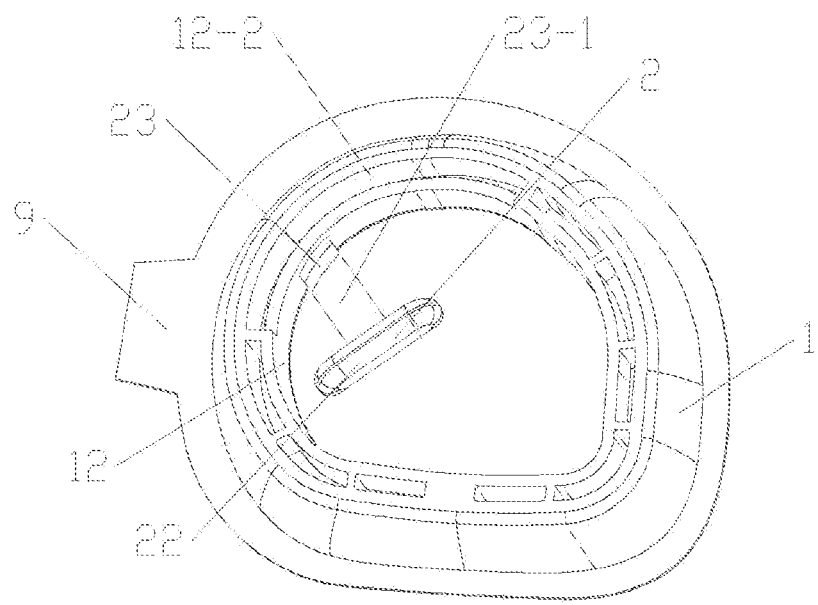
Figure 2:
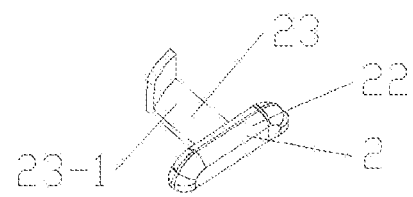
Figure 3:
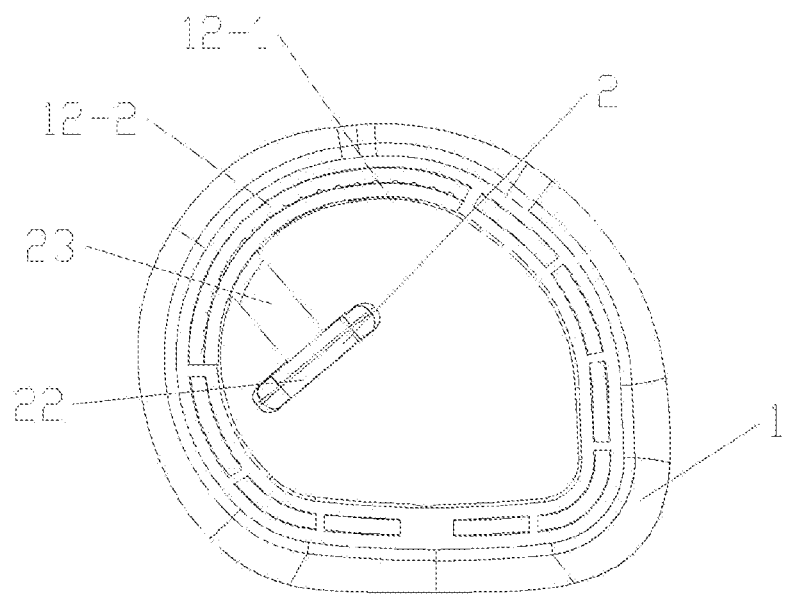
Figures 1, 3:
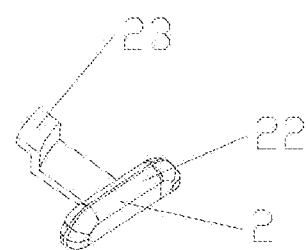
Figure 4:
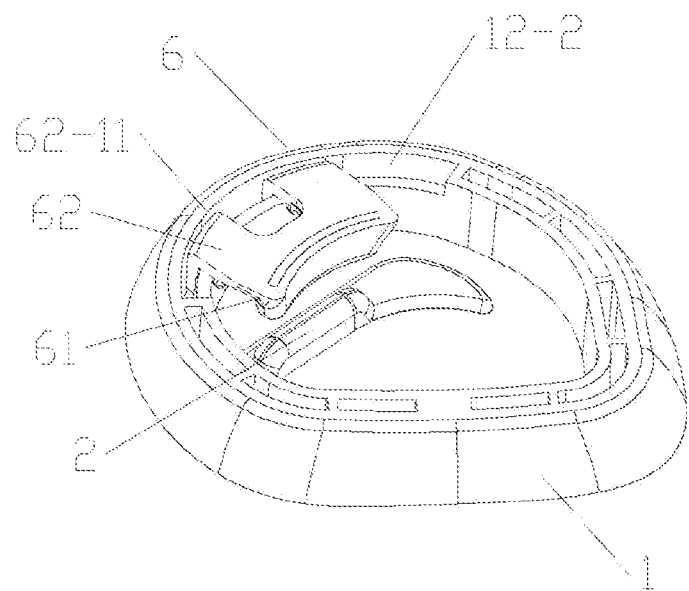
Figures 1, 4:
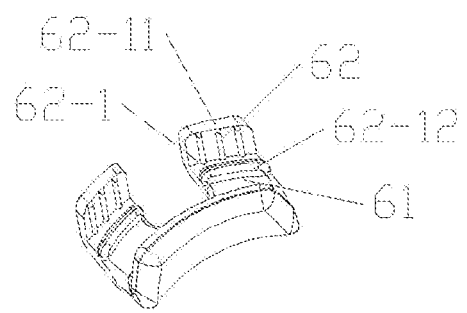

Referring to FIG. 1 to FIG. 1-4, in this embodiment, the adjustable ear shaping mechanism 100 includes a base 1, an ear back support 2, and an upper cover 3.

Figure 7:
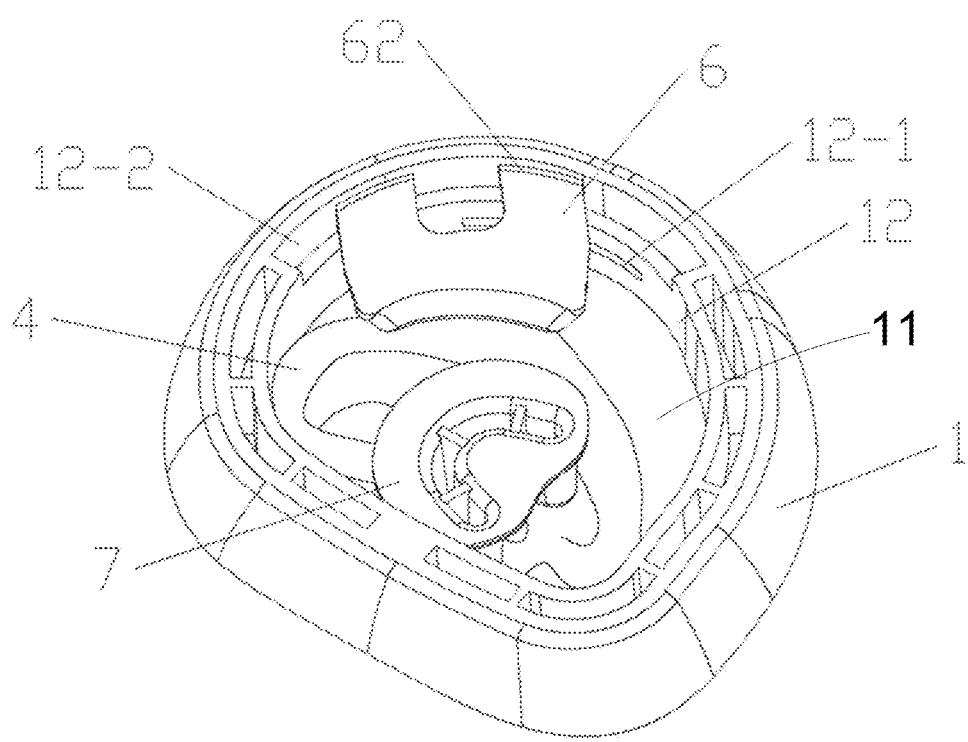
FIG. 7 is a view depicting a working principle of an adjustable ear shaping mechanism of the present application.

Referring to FIG. 7, an opening 11 is provided on the base 1, and the opening 11 allows an ear 4 to pass therethrough. The ear back support 2 is movably disposed in the opening 11, and supports an auricle from the back of the ear 4 according to a part needing orthopedics.

Referring to FIG. 1-2 and FIG. 1-3, the ear back support 2 includes a support portion 22 and a connecting end 23. The support portion 22 can support the auricle from the back of the ear 4, and the connecting end 23 fixes the ear back support 2 on an orthopedic part.

The ear back support 2 selects a part needing support according to a morphological feature of the ear, and then a medical tape is used. Preferably, a double-sided medical tape 9 is used to paste the connecting end 23 on the skin of the part needing support at the back of the ear 4, to position the ear back support 2. When the part needing orthopedics changes, the double-sided medical tape 9 can be torn off to re-fix the ear back support 2 on a different part, which may be adjusted according to a treatment process during clinical use.

The upper cover 3 is detachably connected to the base 1, and an object-containing space 5 is formed between the upper cover 3, the base 1, and the ear back support 2.

In this embodiment, the base 1 is fixed on skin of a periphery of the ear 4 by pasting by the double-sided medical tape 9. One side of the double-sided medical tape 9 is pasted on the bottom of the base 1, and the other side is pasted on the skin. When needing to be replaced, the double-sided medical tape 9 is torn off, and the use process is very convenient. Certainly, in a practical application, those skilled in the art may also use other fixing manners to fix the base 1 on the periphery of the ear as required.

Referring to FIG. 6, an elastic groove 21 is provided on the ear back support 2. The ear back support 2 is arranged behind the ear 4, and the base 1 is fixed at the front of the ear 4 by the upper cover 3. A space height behind the ear is different for everyone. If the space height behind the ear is small, and an excessively large height of the ear back support 2 is likely to cause ischemic necrosis of the ear under an external force, resulting in an accidental injury during an orthopedic process. The elastic groove 21 may be contracted under the external force and reset after the external force is released. Therefore, when the space height behind the ear is small, under the external force, the elastic groove 21 is compressed, and the space increases, so that the elastic groove may adapt to different space heights behind the ear, and clinical use is safer.

Referring to FIG. 4 and FIG. 4-1, in this embodiment, the adjustable ear shaping mechanism 100 further includes a helix former 6. The helix former 6 may be used for helix orthopedics, and especially suitable for forming a rolled rim of the helix.

The helix former 6 includes a forming groove 61 and a fixing portion 62, and the fixing portion 62 and the base 1 are connected. The forming groove 61 is inlaid on the helix to perform orthopedics on the rolled rim of the helix. The fixing portion 62 and the base 1 are connected, which may prevent the helix former 6 from moving and maintain the stability of the orthopedic process.

In this embodiment, the fixing portion 62 is connected to the base 1 by a combination of pasting and inlaying. The fixing portion 62 includes a clamping groove 62-1, a limiting groove 12-2 is provided on an upper end portion of a side wall 12 of the base 1, and an outer leg 62-11 of the clamping groove 62-1 is inserted into the limiting groove 12-2. The double-sided medical tape 9 is provided on an inner side of the side wall 12, and an inner leg 62-12 of the clamping groove 62-1 is pasted on the side wall 12 to form double positioning.

Certainly, in a practical application, those skilled in the art may further design different connection manners as required. The applicant does not give specific examples herein, which do not depart from the protection scope of the present application.

Referring to FIG. 5 and FIG. 5-1, the adjustable ear shaping mechanism 100 further includes an auricular concha former 7. The auricular concha former 7 is designed according to a shape feature of a cavity of auricular concha, and can be used for orthopedics of the cavity of auricular concha. During clinical use, a shaping end 71 of the auricular concha former 7 is plugged into an ear canal, and then the auricular concha former 7 is fixed in the object-containing space 5 by the upper cover 1, referring to FIG. 7.

The base 1 is made of a flexible medical material.

The flexible material is silicone, rubber, thermoplastic elastomer (TPE), or thermoplastic polyurethane (TPU) elastomer rubber.

The adjustable ear shaping mechanism of the present application is usually clinically used for ear orthopedics of newborns, and skin of the newborns is very delicate and sensitive. Therefore, the base 1 in contact with the skin is made of the medical flexible material to ensure comfort. Preferably, the adjustable ear shaping mechanism of the present application is made of the medical flexible material as a whole.

Referring to FIG. 7, during clinical use, first, according to a morphological feature of an ear malformation, a position for mounting the ear back support 2 is selected, and then the ear back support 2 is pasted on skin of a part needing support by the double-sided medical tape 9. Then the base 1 is mounted on the periphery of the ear 4, and the ear 4 extends from the opening of the base 1. In addition, the base 1 is fixed on the skin of the periphery of the ear 4 by the double-sided medical tape 9, and is covered by the upper cover 3. The object-containing space 5 is formed between the upper cover 3, the base 1, and the ear back support 2, and the ear 4 is placed in the object-containing space 5. Meanwhile, the upper cover 3 stretches the base 1 around, to realize traction and orthopedics of the ear 4.

The ear back support 2 of the adjustable ear shaping mechanism of the present application is designed as movable. In a clinical use process, the ear back support 2 may be disposed at a corresponding malformed part behind the ear according to a malformed part of the ear, and support the auricle from the back of the ear 4. During clinical use, the ear back support 2 is fixed at the corresponding malformed part, then the ear 4 extends from the opening 11 of the base, and the base 1 is fixed on a periphery the ear 4. Then, the upper cover 3 covers the base 1, and the ear 4 is fixed in the object-containing space 5, so that an orthopedic treatment can be performed.

The ear back support is designed as movable, and in clinical use, various parts may be selected for fixing according to an ear structure of each patient, thereby effectively preventing the ear 4 from undergoing compression or even ischemic necrosis caused because the ear back support 2 and the helix former 6 are arranged too closely. The clinical use process is safer, and the scope of application is wider.

Embodiment 2: Adjustable Ear Shaping Mechanism of the Present Application with an Ear Back Support Connected to a Side Wall Referring to FIG. 2 to FIG. 2-2, the difference between this embodiment and Embodiment 1 is that the ear back support 2 in this embodiment is connected to a side wall 12 of the base 1.

Referring to FIG. 2 to FIG. 2-2, the ear back support 2 includes a support portion 22 and a connecting end 23, and the connecting end 23 is pasted with the double-sided medical tape 9. The ear back support 2 is pasted on the side wall 12 of the base 1 by the double-sided medical tape 9. The ear back support 2 is pasted on the side wall of the base 1, and does not need to be directly pasted on the surface of the skin, which reduces a risk of possible skin allergy and is safer. Certainly, to ensure stable positioning, a lower surface of a connecting bridge 23-1 of the connecting end 23 may be fixed on the skin by pasting.

During clinical use, first, according to a morphological feature of an ear malformation, a position for mounting the ear back support 2 is selected, and the ear back support 2 is temporarily fixed by a hand, or the connecting bridge 23-1 of the ear back support 2 is pasted on the skin for fixing. Then the base 1 is mounted on a periphery of the ear 4, and the ear 4 extends from the opening of the base 1. After the base 1 is fixed by the double-sided medical tape 9, the ear back support 2 is fixed on the side wall 12 of the base 1.

Referring to FIG. 3 and FIG. 3-1, the ear back support 2 may alternatively be connected to the side wall 12 of the base 1 by inlaying. Different connecting grooves 12-1 may be provided on the side wall 12 of the base 1, and the connecting end 23 of the ear back support may be inlaid in the connecting groove 12-1. The ear back support 2 may be inlaid in a different connecting groove 12-1 as required, or slide back and forth in the connecting groove 12-1 to adjust the position of the ear back support 2. In this way, clinical use is more convenient.

Embodiment 3: Adjustable Ear Shaping Mechanism of the Present Application Including an Auricle Former Referring to FIG. 8 to FIG. 8-2, the difference between this embodiment and Embodiment 1 and Embodiment 2 is that the adjustable ear shaping mechanism in this embodiment further includes an auricle former 8.

The auricle former 8 is designed according to a shape feature of a normal ear, and is arranged at the front of the ear 4 when in use.

The auricle former 8 includes a helix forming mechanism 81, and/or an antihelix forming mechanism 82, and/or a triangular fossa forming mechanism 83, and/or an auricular concha forming mechanism 84, and/or a tragus forming mechanism 85, and/or an antitragus forming mechanism 86. One or more of the foregoing forming mechanisms may be provided on the auricle former 8 as required.

The auricle former 8 and the ear back support 2 are matched with each other, and a space therebetween is in a shape of the normal ear, and meanwhile forms a forming space of the ear 4.

In this embodiment, the auricle former 8 and the upper cover 3 may be integrally made. The auricle former 8 may alternatively be disposed separately and then covered by the upper cover 3.

To ensure auditory sensation of children patients, through holes are provided on the auricle former 8 and the upper cover 3 to ensure sound conduction.

Figure 8:
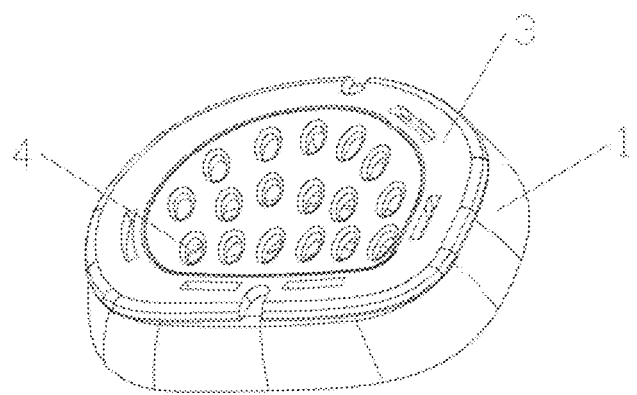
FIG. 8 is a schematic three-dimensional structural diagram of an adjustable ear shaping mechanism of the present application including an auricle former.
Figures 1, 8:
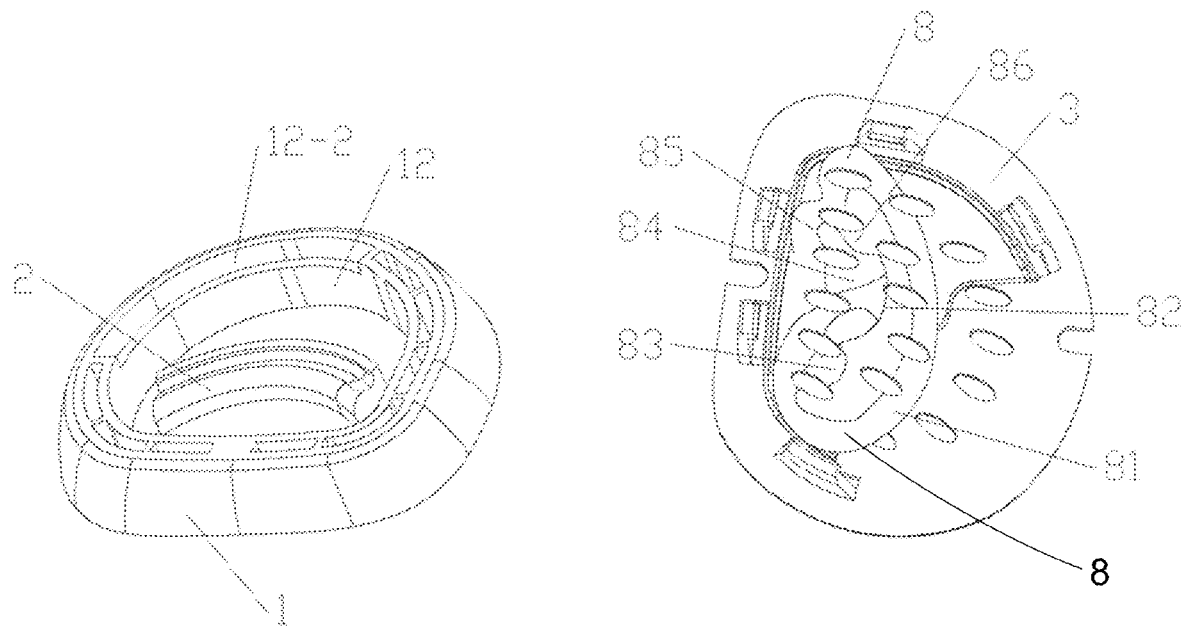
Figures 2, 8:
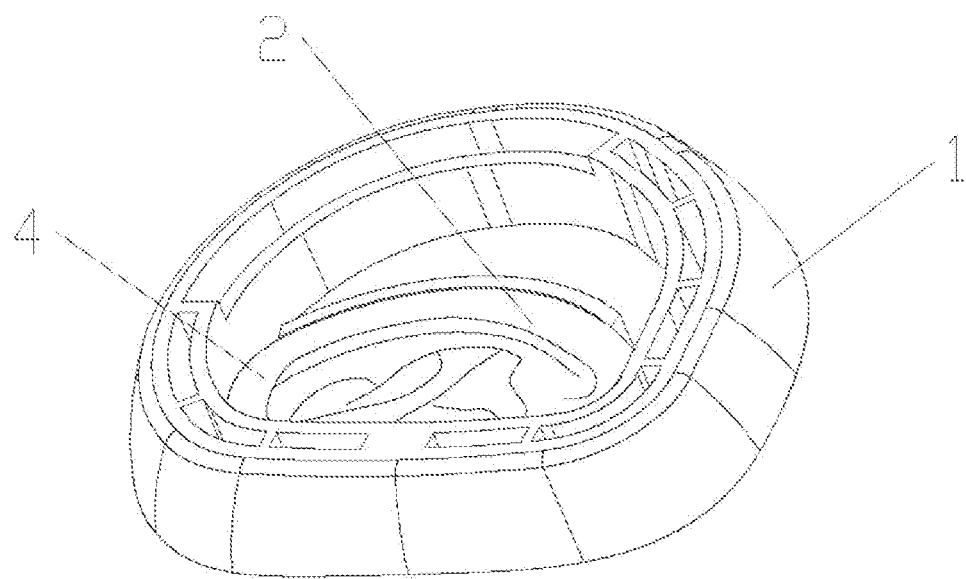

Referring to FIG. 8 and FIG. 8-2, during clinical use, first, the ear back support 2 is fixed in a suitable position, and then the base 1 is fixed on the periphery of the ear 4. The ear extends from the opening 11 of the base 1, and the auricle former 8 and the upper cover 3 that are integrally made are then mounted on the base 1. The object-containing space 5 in the morphology of the normal ear is formed between the auricle former 8 and the ear back support 2, and the ear 4 can grow and be shaped in the object-containing space 5.

In this embodiment, overall shaping may be performed on the ear 4 through mutual cooperation between the auricle former 8 and the ear back support 2, so that the orthopedics on the whole ear can be completed at a time in the clinical use process. The helix forming mechanism 81, the antihelix forming mechanism 82, the triangular fossa forming mechanism 83, the auricular concha forming mechanism 84, the tragus forming mechanism 85, and the antitragus forming mechanism 86 are designed according to morphological features of the normal ear. Therefore, in the orthopedic process, the helix forming mechanism 81, the antihelix forming mechanism 82, the triangular fossa forming mechanism 83, the auricular concha forming mechanism 84, the tragus forming mechanism 85, and the antitragus forming mechanism 86 can fit the shape of each part to form surface contact, to change an orthopedic manner in which the helix is partially expanded and pulled outwards in the prior art into a surface contact three-dimensional space traction orthopedic manner. In this way, a pressure intensity at a contact part is reduced, and tissue compression and necrosis are less likely to occur. In addition, for the manner of space multipoint traction, only a very small force is needed to achieve an intended aim of orthopedics, a clinical use process is safer, and an orthopedic effect is better.

It should be noted that the structure disclosed and described in this specification may be replaced with another structure with the same effect. In addition, the embodiments described in the present application are not the only structure of implementing the present application. Although preferable embodiments of the present application are already introduced and illustrated in the specification, it is clearly known by a person skilled in the art that the embodiments are merely described by way of example, and a person skilled in the art may make various changes, improvements, and replacements without departing from the present application. Therefore, the protection scope of the present application should be defined in accordance with the spirit and scope of the claims appended to the present application.

What is claimed is:

1. An adjustable ear shaping mechanism, comprising:
a base, the base including an opening adapted to receive an ear of a user therethrough;
an ear back support, wherein the ear back support:
is movably disposed in the opening;
is located adjacent to a side wall of the base, being adjustable to different positions relative to the base; and
is adapted to support an auricle of the ear from a back of the ear;
a cover detachably connected to the side wall of the base, wherein the cover, the base, and the ear back support define a cavity that includes the opening; and
an auricle former, wherein the auricle former is adapted to be arranged at a front of the ear and is adapted to match the ear back support defining a space for shaping the ear.

2. The adjustable ear shaping mechanism according to claim 1, wherein the base is adapted to be fixed on a skin at a periphery of the ear by pasting.

3. The adjustable ear shaping mechanism according to claim 1, wherein the ear back support is adapted to be pasted on a skin behind the ear for fixing.

4. The adjustable ear shaping mechanism according to claim 1, wherein the auricle former and the cover are integrally made.

5. The adjustable ear shaping mechanism according to claim 1, wherein the ear back support is connected onto the side wall of the base by pasting or inlaying.

6. The adjustable ear shaping mechanism according to claim 1, wherein an elastic groove is provided on the ear back support.

7. The adjustable ear shaping mechanism according to claim 1, wherein the adjustable ear shaping mechanism further comprises a helix former.

8. The adjustable ear shaping mechanism according to claim 7, wherein the helix former comprises a forming groove and a fixing portion, and the fixing portion is connected to the base.

9. The adjustable ear shaping mechanism according to claim 8, wherein the fixing portion is connected to the base by pasting or inlaying.

10. The adjustable ear shaping mechanism according to claim 1, wherein the adjustable ear shaping mechanism further comprises an auricular concha former configured to be inserted into an ear canal of the ear.

11. The adjustable ear shaping mechanism according to claim 1, wherein the base is made of a flexible medical material.

12. The adjustable ear shaping mechanism according to claim 11, wherein the flexible medical material is silicone, rubber, thermoplastic elastomer (TPE), or thermoplastic polyurethane (TPU) elastomer rubber.

13. The adjustable ear shaping mechanism according to claim 1, wherein the auricle former comprises a helix forming mechanism, and/or an antihelix forming mechanism, and/or a triangular fossa forming mechanism, and/or an auricular concha forming mechanism, and/or a tragus forming mechanism, and/or an antitragus forming mechanism.

14. An adjustable ear shaping mechanism, comprising:
a base, the base including an opening adapted to receive an ear of a user therethrough;
an ear back support, wherein the ear back support:
is movably disposed in the opening;
is located adjacent to a side wall of the base, being adjustable to different positions relative to the base; and
is adapted to support an auricle of the ear from a back of the ear, wherein an elastic groove is provided on the ear back support; and
a cover detachably connected to the side wall of the base, wherein the cover, the base, and the ear back support define a cavity that includes the opening.

15. An adjustable ear shaping mechanism, comprising:
a base, the base including an opening adapted to receive an ear of a user therethrough;
an ear back support, wherein the ear back support:
is movably disposed in the opening;
is located adjacent to a side wall of the base, being adjustable to different positions relative to the base; and
is adapted to support an auricle of the ear from a back of the ear;
a cover detachably connected to the side wall of the base, wherein the cover, the base, and the ear back support define a cavity that includes the opening; and
a helix former, the helix former comprising a forming groove and a fixing portion, and the fixing portion is connected to the base.

* * * * *